US010993692B2

(12) United States Patent
Spiegel (10) Patent No.: US 10,993,692 B2
(45) Date of Patent: May 4, 2021

(54) METHODS FOR PREDICTION OF POSTOPERATIVE ILEUS (POI)

(71) Applicant: Cedars-Sinai Medical Center, Los Angeles, CA (US)

(72) Inventor: Brennan Spiegel, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 370 days.

(21) Appl. No.: 15/777,123

(22) PCT Filed: Dec. 8, 2016

(86) PCT No.: PCT/US2016/000120
§ 371 (c)(1),
(2) Date: May 17, 2018

(87) PCT Pub. No.: WO2017/099816
PCT Pub. Date: Jun. 15, 2017

(65) Prior Publication Data
US 2018/0333133 A1 Nov. 22, 2018

Related U.S. Application Data

(60) Provisional application No. 62/264,406, filed on Dec. 8, 2015.

(51) Int. Cl.
*A61B 7/00* (2006.01)
*A61B 5/00* (2006.01)
(Continued)

(52) U.S. Cl.
CPC ............ *A61B 7/008* (2013.01); *A61B 5/0004* (2013.01); *A61B 5/1107* (2013.01);
(Continued)

(58) Field of Classification Search
CPC ... A61B 7/0008; A61B 5/0004; A61B 5/1107; A61B 5/1126; A61B 5/4255;
(Continued)

(56) References Cited

U.S. PATENT DOCUMENTS 5,301,679 A 4/1994 Taylor
2002/0156398 A1 10/2002 Mansy
(Continued)

FOREIGN PATENT DOCUMENTS

CN 105758949 A 7/2016
WO WO-2014039404 A1 * 3/2014 ........... A61B 5/1135
(Continued)

OTHER PUBLICATIONS

Spiegel, Brennan M. R., et al. "Validation of an Acoustic Gastrointestinal Surveillance Biosensor for Postoperative Ileus." Journal of Gastrointestinal Surgery, vol. 18, No. 10, 2014, pp. 1795-1803., doi:10.1007/s11605-014-2597-y (Year: 2014).*
(Continued)

*Primary Examiner* — Daniel L Cerioni
(74) *Attorney, Agent, or Firm* — Nixon Peabody LLP (57) ABSTRACT

Described herein is a method employing acoustic data from a patient's abdominal cavity to predict potential onset of postoperative ileus (POI) in patients recovering from surgery. According to one embodiment of the method, the rate of intestinal motility events, as well as the change in the rate across specific time periods, is analyzed to predict, or rule out, potential onset of POI. The current risk assessment may then be reported, and used to determine a course of treatment, such as rapidly advancing diet in low risk patients according to enhanced recovery after surgery protocols. The method can be applied at the patient's bedside by a nurse or other medical provider, and used to determine the POI risk assessment for the patient.

18 Claims, 7 Drawing Sheets

(51) Int. Cl.
  *A61B 5/11* (2006.01)
  *A61B 7/02* (2006.01)
  *A61B 7/04* (2006.01)
(52) U.S. Cl.
  CPC .......... *A61B 5/1126* (2013.01); *A61B 5/4255* (2013.01); *A61B 5/486* (2013.01); *A61B 5/6823* (2013.01); *A61B 5/7275* (2013.01); *A61B 5/743* (2013.01); *A61B 7/026* (2013.01); *A61B 7/04* (2013.01); *A61B 2562/0204* (2013.01); *A61B 2562/028* (2013.01)
(58) Field of Classification Search
  CPC ..... A61B 5/486; A61B 5/6823; A61B 5/7275; A61B 5/743; A61B 7/026; A61B 7/04; A61B 2562/0204; A61B 2562/028
  See application file for complete search history.

(56) References Cited

U.S. PATENT DOCUMENTS

| | | | |
|---|---|---|---|
| 2003/0153847 A1* | 8/2003 | Sandler | A61B 7/008 600/587 |
| 2006/0199155 A1 | 9/2006 | Mosher | |
| 2007/0238995 A1* | 10/2007 | Sui | A61B 5/021 600/437 |
| 2008/0306355 A1 | 12/2008 | Walker | |
| 2010/0228105 A1 | 9/2010 | Policker | |
| 2011/0056264 A1 | 3/2011 | Kaplan | |
| 2011/0257490 A1* | 10/2011 | Semler | A61B 5/073 600/301 |
| 2012/0116186 A1* | 5/2012 | Shrivastav | A61B 5/4803 600/301 |
| 2013/0035610 A1* | 2/2013 | Cromwell | A61B 7/008 600/586 |
| 2014/0348370 A1 | 11/2014 | Fortemedia | |
| 2015/0250445 A1 | 9/2015 | Spiegel | |
| 2017/0055871 A1* | 3/2017 | Axelrod | A61B 7/008 600/587 |

FOREIGN PATENT DOCUMENTS

| | | |
|---|---|---|
| WO | WO 2016/112127 A1 | 7/2016 |
| WO | 2017099816 A1 | 6/2017 |

OTHER PUBLICATIONS

International Search Report and Written Opinion of PCT/US2016/000120, dated Mar. 16, 2017, 13 Pages.
International Search Report and Written Opinion of International Searching Authority for Application No. PCT/US2018/030678, dated Jul. 19, 2018 (12 pages).
Extended European Search Report for Application No. EP 16783485.3, dated Jul. 23, 2019 (10 pages).

* cited by examiner

| Characteristic | Patients with POI (n = 9) | Patients without POI (n = 19) |
|---|---|---|
| Age - Mean (SD) | 53.4 (11.37) | 44.68 (14.47) |
| Male Gender - N (%) | 5 (56%) | 10 (53%) |
| Race - N (%) White Black Hispanic / Other | 7 (78%) 1 (11%) 1 (11%) | 12 (63%) 3 (16%) 4 (21%) |
| BMI - Mean (SD) | 25.97 (6.34) | 21.74 (4.0) |
| Type of Surgery Small bowel surgery Partial colectomy Total colectomy Pelvic surgery (APR, LAR, IPAA) Other | 2 (22%) 3 (33%) 3 (33%) 1 (11%) 0 (0%) | 8 (42%) 5 (26%) 1 (5%) 4 (21%) 1 (5%) |
| Indication for surgery Colorectal cancer / polyp Inflammatory Bowel Disease Ileostomy Takedown Other | 3 (33%) 2 (22%) 2 (22%) 2 (22%) | 6 (32%) 3 (16%) 7 (37%) 3 (16%) |

METHODS FOR PREDICTION OF POSTOPERATIVE ILEUS (POI)

CROSS-REFERENCE TO RELATED APPLICATIONS

This application is a National Phase of International Application No. PCT/US2016/000120 filed Dec. 8, 2016, which designated the U.S. and that International Application was published under PCT Article 21(2) in English, which also includes a claim of priority under 35 U.S.C. § 119(e) to U.S. provisional patent application No. 62/264,406 filed Dec. 8, 2015, the entirety of which is hereby incorporated by reference.

TECHNICAL FIELD

Provided herein are methods and systems for monitoring acoustical activity from the abdominal cavity of a patient and predicting potential onset of postoperative ileus (POI).

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Bowel paralysis is a prevalent and expensive condition following a wide range of surgeries, particularly those involving the abdominal cavity.[1-3] When prolonged or complicated, postoperative ileus (POI) can worsen patient outcomes, increase cost of care, and lengthen the hospital stay.[4,5] Delayed oral feeding can lead to poor wound healing, increased infection, or need for parenteral nutrition.[1] Because of the high prevalence and impact of POI, the condition costs over $1.75 billion annually in the U.S.[4,5]

Use of Enhanced Recovery After Surgery (ERAS) protocols have led to measurable improvements in outcomes following abdominal surgery.[6-9] These protocols expedite postoperative feeding so patients can eat quickly and be discharged rapidly. Although ERAS protocols are generally safe and reduce length of stay, between 4 and 25% of patients cannot tolerate feeding and require nasogastric tube decompression or bowel rest.[10-14] When this occurs it can lead to patient complications, increased hospital stay, increased costs, and even death.

Monitoring for development of POI is generally imprecise and subjective. Clinical assessments rely on observation, intermittent physical examination, assessments for flatus (e.g. "passing gas") or stool passage, and use of a stethoscope to monitor bowel sounds. If needed, clinicians may obtain an abdominal X-Ray or CT scan to look for signs of POI, such as distended intestines, but these methods are expensive, time consuming, and resource intensive. Additionally, it requires the patient to be exposed to radiation, and specialized technicians are required to review the findings.

Thus, there is an unmet need for an objective marker that could predict which patients are at risk of developing POI and which patients will uneventfully recover GI function. Such a capability could help medical staff expedite recovery for low risk patients, yet delay feeding or make other adjustments to treatment for those patients likely to experience complications.

SUMMARY

The following embodiments and aspects thereof are described and illustrated in conjunction with systems, compositions and methods which are meant to be exemplary and illustrative, not limiting in scope.

According to aspects of the present disclosure, a method for assessing risk of postoperative ileus for a patient recovering from surgery is presented. According to the method, at least one processor receives acoustic signal data from one or more sensors, each of which is in contact with the patient and able to capture acoustic signals from the patient's abdominal cavity. The at least one processor analyzes the acoustic signal data to determine digestive metric(s). A risk assessment score is determined according to the digestive metric(s), and a report of potential postoperative ileus risk, including the risk assessment score, is displayed on a display device in communication with the at least one processor.

According to further aspects of the present disclosure, a method of determining risk of ileus for a patient following surgery, and administering a treatment according to the determined risk to expedite recovery for patients with lower predicted risk of ileus, while reducing complications for patients with higher predicted risk of ileus is presented. Per the method, the patient's intestinal rate is continuously measured over a fixed time period, the fixed time period including the time period from the first postoperative day to the second postoperative day. The intestinal rate measurements are analyzed to generate prediction data that includes a comparison of the median intestinal rate of the patient for the first postoperative day with the median intestinal rate of the patient for the second postoperative day. The patient's expected risk of ileus is determined according to the prediction data, and for patients with lower expected risk, an aggressive feeding protocol is administered. For patients with higher expected risk, feeding is restricted.

According to still further aspects of the present disclosure, a further method of determining risk of ileus for a patient following surgery, and administering a treatment according to the determined risk to expedite recovery for patients with lower predicted risk while reducing complications for patients with higher predicted risk is presented. Per the method, one or more sensors are attached to the patient. Using the sensors, an intestinal rate of the patient is continuously measured during a first postoperative day to obtain a first plurality of intestinal rate measurements. A first mean intestinal rate value is determined for the first postoperative day based on the first plurality of intestinal rate measurements. The one or more sensors are further used to continuously measure the intestinal rate of the patient during a second postoperative day to obtain a second plurality of intestinal rate measurements. A second mean intestinal rate value for the second postoperative day is determined based on the second plurality of intestinal rate measurements. A change in mean intestinal rate value based on the first mean intestinal rate value and the second mean intestinal rate value is calculated. The first plurality of intestinal rate measurements and the second plurality of intestinal rate measurements are analyzed to calculate a percentage of intestinal rate measurements below a threshold intestinal rate. The risk of ileus for the patient is then determined based at least on the calculated change in mean intestinal rate and the calculated percentage of intestinal rate measurements below the threshold intestinal rate. The determined risk of ileus for the patient is continuously updated. A patient determined to have a lower expected risk of ileus is administered an aggressive feeding protocol, while a patient determined to have a higher expected risk of ileus is administered a restricted feeding protocol.

These and other capabilities of the invention, along with the invention itself, will be more fully understood after a review of the following figures, detailed description, and claims.

BRIEF DESCRIPTION OF THE DRAWINGS

Exemplary embodiments are illustrated in referenced figures. It is intended that the embodiments and figures disclosed herein are to be considered illustrative rather than restrictive.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

All references cited herein are incorporated by reference in their entirety as though fully set forth herein. Unless defined otherwise, technical and scientific terms used herein have the same meaning as commonly understood by one of ordinary skill in the art to which this disclosure belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

As noted above, there is a need for an objective marker that could easily predict which patients are developing postoperative ileus (POI) and which patients will uneventfully recover GI function. Therefore, disclosed herein are methods that employ acoustic data from the abdominal cavity to predict early onset of POI in patients recovering from surgery. POI is a common and expensive postoperative condition marked by intestinal paralysis and food intolerance. Patients that have developed POI have difficulty advancing food, and can often suffer from unexpected vomiting. Radiographic evidence of bowel distension may also indicate the development of POI.

The method evaluates dynamic changes in acoustic intestinal rate (IR), defined as motility events per minute, to predict onset of POI. A motility event is a contraction or similar event in the esophagus, stomach, or any other organ of the digestive system that produces a distinctive acoustic signature. Using receiver operator characteristic (ROC) curve analysis, the method discriminates between POI and non-POI patients and presents the results to a healthcare provider, who can then make an evidence-based decision about whether and how to feed the postoperative patient. Appropriate postoperative feeding can improve safety, reduce complications, and reduce length of stay in the hospital compared to inappropriate feeding decisions.

The method may be applied using one or more biosensor(s) to measure abdominal sounds and communicate the acoustic data to a processor for further analysis and reporting. According to some embodiments, one or more Acoustic Gastrointestinal Surveillance (AGIS) biosensors may be employed to collect acoustic information from the patient for evaluation.[15] The acoustic information may then be measured to generate IR data, which can be further analyzed according to the methods herein.

The method uses IR data prospectively to identify early warning signs of evolving POI. For example, the change in mean IR between postoperative day 1 (POD#1) and postoperative day 2 (POD#2) is a significant and early predictor of POI. This may be a useful and objective biomarker because it can be calculated and recognized early in the postoperative course, providing the opportunity for early intervention. If the IR is falling between these days, then it may portend POI and the surgeon should consider delaying diet advancement, reducing use of narcotics if possible, or both. Additionally, if a patient exhibits very low IR values for extended periods of time—such as less than 1.5 motility events per minute—this also indicates increased risk of POI.

Thus, as further detailed below, the method evaluates the ratio of the mean IR for POD#1 in comparison with the mean IR for POD#2, and also measures the percentage of time the subject maintains an IR of 1.5 events per minute, or less. By combining these two metrics, the method can predict onset of POI with a sensitivity, specificity, and negative predictive value of 63%, 72%, and 81%, respectively, based on initial testing. This is superior to the current, non-objective approach to monitoring for POI, discussed later in this document. The method may also be applied to rule-out POI with a high degree of certainty. In particular, data supporting this disclosure reveals that the surgical team can rule-out evolving POI with a negative predictive value of 81%. In this scenario, the method may provide further confidence to advance the diet according to ERAS protocols and expedite discharge where possible.

According to some embodiments, the predicted POI risk is reported via a graphical user interface to a provider, who then makes decisions about whether and how to feed a patient. The method provides the benefit of continuous analysis of IR data, and, in some embodiments, the method can report the instantaneous risk for the patient. Thus, through capture, analysis, and application of IR data, better clinical outcomes can be achieved during surgical recovery.

Figure 1:
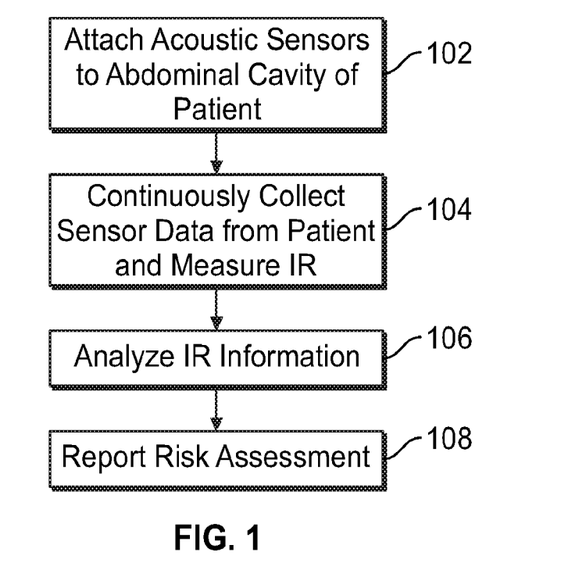
FIG. 1 depicts in accordance with various embodiments of the disclosure, an exemplary process flow for predicting a patient's risk of POI.
Figure 2A:
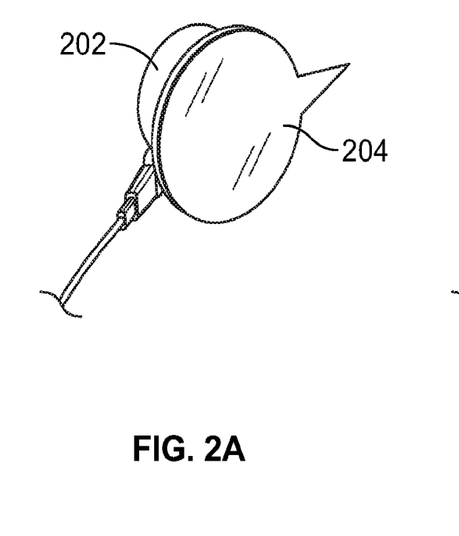
FIGS. 2A and 2B depict in accordance with various embodiments of the disclosure, a sensor to monitor acoustic data from a patient.
Figure 2B:
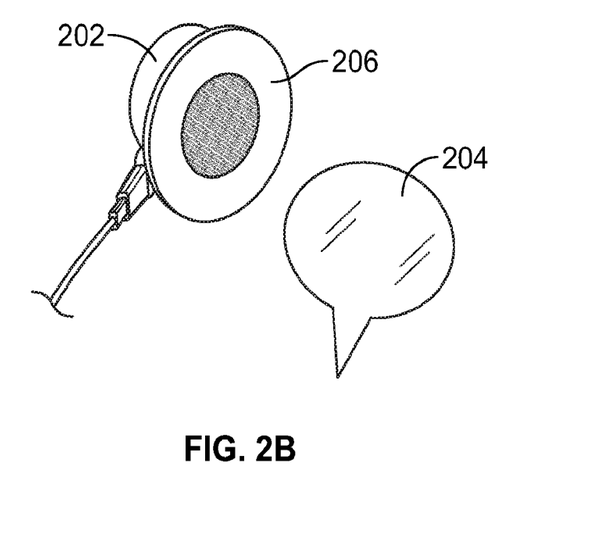

Turning to FIG. 1, an exemplary method for evaluating a patient's risk for developing POI is detailed. At 102, one or more sensors are placed on the patient's abdominal region, to monitor acoustic data from the abdominal cavity. The sensors include one or more standard microelectric microphones that adhere to the abdominal wall, and collect and transmit acoustic data to a processor for further analysis. According to some embodiments, the sensors may be of the type disclosed in WO2014/039404 A1 "Multisensor Wireless Abdominal Monitoring Apparatus, Systems, and Methods," or as shown in FIGS. 2A and 2B. FIG. 2A illustrates an acoustic sensor 202 having a protective film 204 disposed thereon. FIG. 2B illustrates the acoustic sensor 202 with the protective film 204 detached, thereby exposing a facing portion 206 that is configured to contact the patient's abdominal region. According to other embodiments, a wireless sensing device could be adapted or modified to perform the methods disclosed herein. One such wireless sensing device that may be adapted is the smart stethoscope, a Bluetooth enabled electronic sensor attached to a stethoscope for monitoring heart sounds, available at www.ekodevices.com.

According to some embodiments, as an optional procedure, the one or more sensors may be placed before surgery, as a baseline measurement for the patient. This may not be desired or practical for patients requiring emergency surgery, or for patients having conditions where the baseline data would not be meaningful due to an acute condition (for example, bowel obstruction). However, if available, the pre-surgery baseline measurements may be useful as a comparison against which to analyze postoperative data. According to some embodiments, the sensors are in place for approximately one hour to collect preoperative acoustical data from the patient, and then are removed in preparation for surgery.

Figure 3:
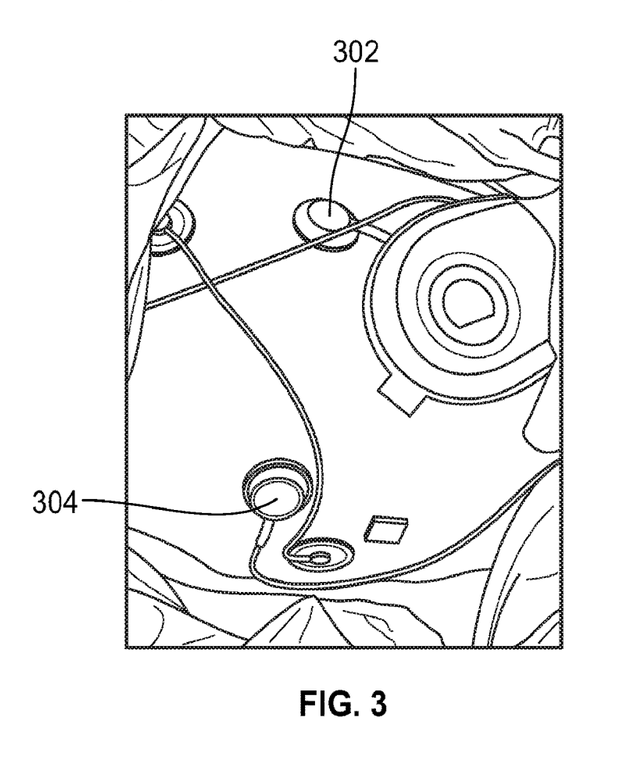
FIG. 3 depicts in accordance with various embodiments of the disclosure, sensors applied to the abdominal region of a postsurgical patient.

During or after surgery, the one or more sensors are placed on the patient to continuously monitor acoustic data from the patient's abdominal region. As shown in FIG. 3, two sensors 302 and 304 have been attached for continuous monitoring of a postsurgical patient.

Although two sensors are shown in FIG. 3, alternative sensor arrangements may be used. According to some embodiments, a single sensor is sufficient if placed within 2-4 cm of the patient's umbilicus. According to other embodiments, having two or more sensors may allow for more precise identification of a signal location within a patient. When using more than one sensor, logic is needed to detect the case where the same auditory signal captured by a plurality of sensors, and correct for this condition so that the signal is only considered once and "double counting" is avoided.

The one or more sensors will capture acoustic data from the patient's bowels. At step 104, this data is then collected and measured to determine the patient's IR over time. IR Data comprises a plurality of IR measurements. Step 104 of FIG. 1 is expanded and illustrated in FIG. 4, where an exemplary method 400 of obtaining an IR measurement is shown. At step 402, corresponding to time t=0, the sensors placed on the patient begin recording acoustic data and counting the number of motility events the patient experiences. The sensors count the number of motility events for a time period $T_{IR}$, which is measured in minutes. At step 404, corresponding to time $t=T_{IR}$, the recorded motility events are summed to obtain the total number of motility events experienced, denoted as $N_{mc}$. At step 406, the individual IR measurement is obtained by dividing $N_{mc}$ by $T_{IR}$.

Figure 4:
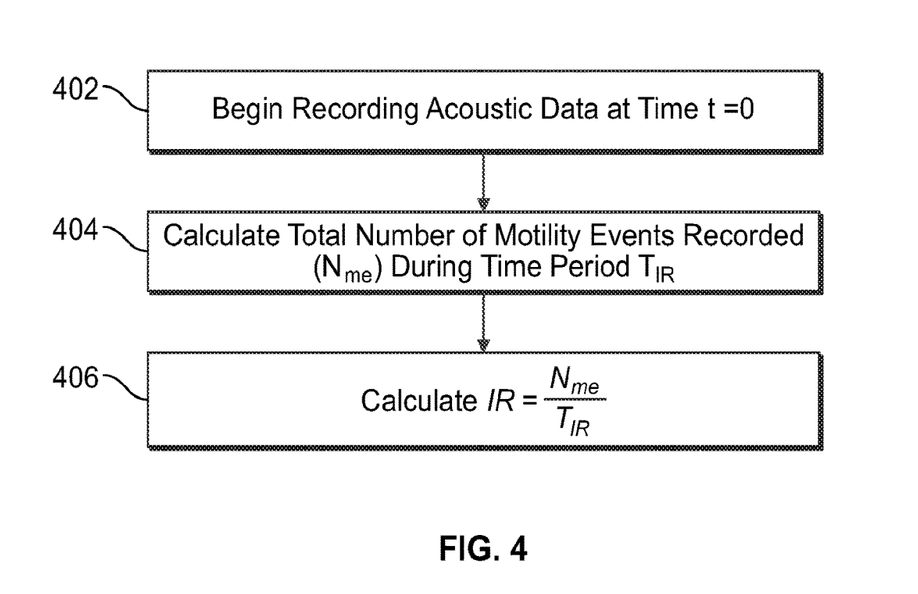
FIG. 4 depicts in accordance with various embodiments of the disclosure, an exemplary process flow for obtaining an intestinal rate measurement of a patient.

An individual IR measurement is thus obtained by recording the number of motility events that occur in a certain time period and dividing that number by the number of minutes in the time period. For example, if twenty motility events are detected ($N_{mc}$=20) over a time period of $T_{IR}$=10 minutes, the single IR measurement would be equal to two motility events per minute. In an exemplary embodiment, time period $T_{IR}$ is any one of 1 minute, 2 minutes, 5 minutes, 10 minutes, 30 minutes, 60 minutes (1 hour), 360 minutes (6 hours), 720 minutes (12 hours), or 1,440 minutes (24 hours). Other time periods are also contemplated.

A mean IR value for an individual day, denoted as $IR_{MEAN}$, may also be calculated by taking the sum of the individual IR measurements for the day and dividing by the number of IR measurements obtained for that day. For example, if a total of N IR measurements are recorded in a day, and each individual IR measurement is denoted as $IR_n$, the mean IR value for the day may be calculated thusly:

$$IR_{MEAN} = \frac{\sum_{n=1}^{N} IR_n}{N}.$$

Figure 5:
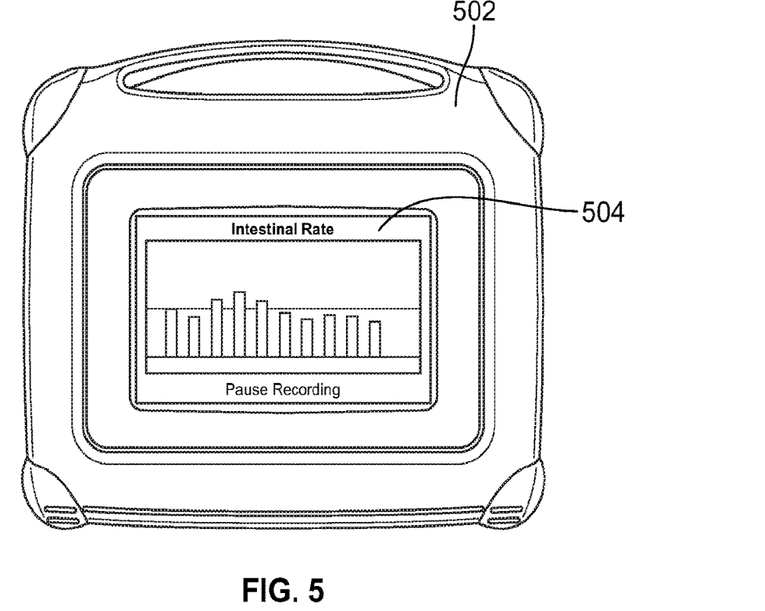
FIG. 5 depicts in accordance with various embodiments of the disclosure, a portable processing device for measuring and displaying intestinal rate data.

According to some embodiments, the acoustic data collected by the one or more sensors is communicated to a processor, such as a bedside computer configured to analyze the acoustic data. The processor may receive the acoustic signal data from the one or more sensors via a wired connection. Alternatively, the one or more sensors may be configured to wirelessly transmit data to the processor, such as by WiFi, Bluetooth, or other wireless capability. The processor may be in the form of a desktop computer, laptop computer, medical appliance, tablet, smart phone, or other processing device capable of receiving real-time acoustic data from the sensor(s), measuring IR, and performing further analysis as detailed below. FIG. 5 illustrates one example of a portable processing device 502 for measuring and reporting IR, and capable of adaptation (for example, via additional software instructions or programming) to perform the IR analysis and reporting as disclosed herein.

According to other embodiments, the processor is remotely located from the one or more sensors, but communicatively coupled to the sensors via a data network. Thus, the processor may be located at a centralized location, such as a monitoring station or nurses' station. In some embodiments, the data network is the Internet, local area network, or a private intranet. Additionally, the data may be encrypted or otherwise secured during transmission.

Referring again to FIG. 1 at 106, the IR measurements are analyzed to determine the patient's POI risk. In some embodiments, the analysis of change in mean IR is used to predict POI. The data from retrospectively applying the analysis to an experimental patient group shows that the change in mean IR between POD#1 and POD#2 is significant in predicting POI. Thus, a comparison of the mean IR value on POD#1 and POD#2 may be performed by dividing the mean POD#2 IR by the mean POD#1 IR. A resulting value greater than 1.0 indicates that the mean IR value is rising from POD#1 to POD#2, whereas a value less than 1.0 indicates a falling mean IR value. A falling value indicates a patent that may potentially be at risk for developing POI.

According to some embodiments, the percentage of total IR measurements that fall below a threshold value is also significant in predicting POI. For example, the analysis of data from an experimental patient group shows that patients with POI spend 40% of the time below a rate of 1.5 motility events per minute. In contrast, the patients without POI only spend 21% of the time below the 1.5 level.

Figure 6:
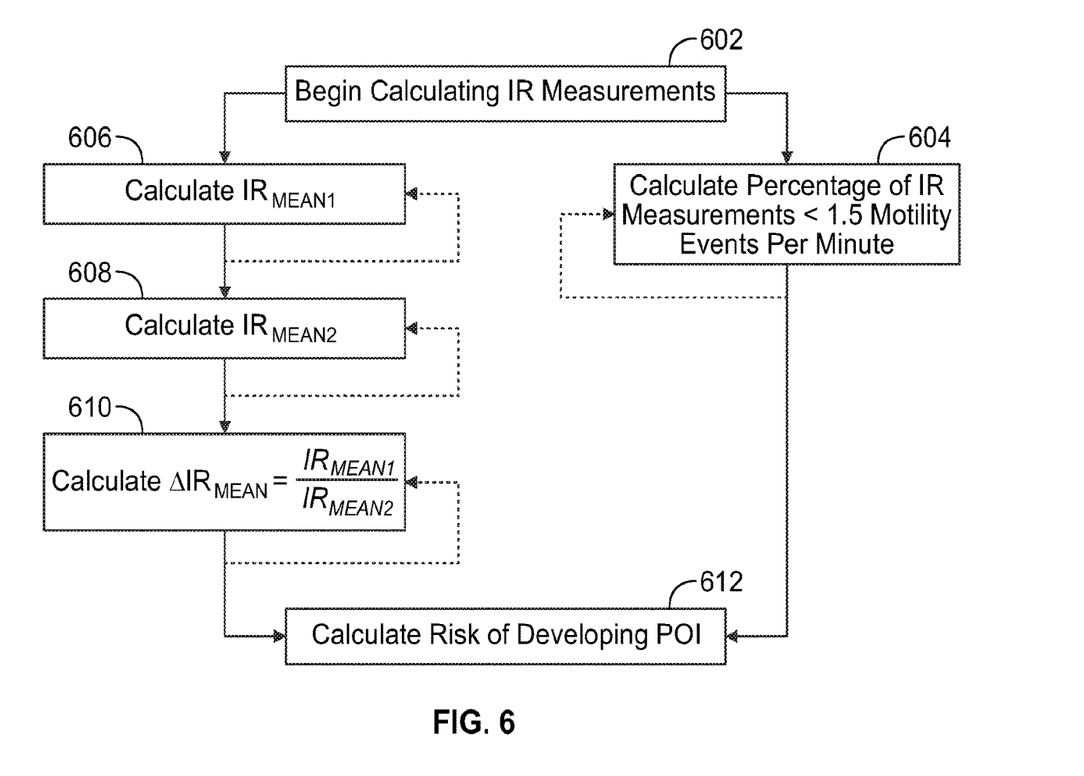
FIG. 6 depicts in accordance with various embodiments of the disclosure, an exemplary process flow for calculating a patient's risk of POI.

In an embodiment, the analysis combines the analyses of the change in mean IR and the percentage of time below a threshold value. The combination of these analyses provides for greater accuracy in predicting POI, as the separate analyses contemplate different features of the IR data. Referring now to FIG. 6, this embodiment of calculating a patient's risk of developing POI is illustrated as method 600. At step 602, the sensors begin recording the acoustic data and the system begins calculating IR measurements. At step 604, the percentage of total IR measurements below a rate of 1.5 motility events per minute is calculated. This percentage may be denoted as % $IR_{<1.5}$. In an exemplary embodiment, this calculation is done in real-time and is continually updated, as indicated by the dashed arrow connecting step 604 to itself. Thus, a new value for the percentage of IR measurements falling below 1.5 motility events per minute is calculated each time a new IR measurement is recorded.

At step 606, the mean IR value for POD#1, denoted as $IR_{MEAN1}$, is calculated. In an exemplary embodiment, this value is calculated at the end of POD#1, as the real-time value of the mean IR value for POD#1 is not required during POD#1. In another embodiment, this calculation is done in real-time and is continually updated. At step 608, the mean IR value for POD#2, denoted as $IR_{MEAN2}$, is calculated. At step 610, the change in mean IR, denoted as $\Delta IR_{MEAN}$, is calculated:

$$\Delta IR_{MEAN} = \frac{IR_{MEAN2}}{IR_{MEAN1}}.$$

Both the $IR_{MEAN2}$ and the $\Delta IR_{MEAN}$ values may be updated in real-time as continual IR measurements are made. Finally, at step 610, both % $IR_{<1.5}$ and $\Delta IR_{MEAN}$ are used as inputs to a logit model that calculates a risk that the patient will develop POI. These two inputs to the logit model are constantly updated each time a new IR measurement is recorded, and thus the patient's risk of developing POI is calculated and provided in real-time to the healthcare provider. In an exemplary embodiment, this risk is expressed as a percentage, with a higher percentage corresponding to a greater risk of developing POI. The logit model is expressed as shown:

$$\ln\left(\frac{P}{1-P}\right) = 0.064(\%IR_{<1.5}) - 2.09(\Delta IR_{MEAN}) - 0.988.$$

Here, P refers to the POI risk percentage—i.e. the probability that the patient will develop POI—while ln X refers to the logarithm of X to base e, otherwise known as the natural logarithm. $\Delta IR_{MEAN}$ is expressed as a decimal, while % $IR_{<1.5}$ is expressed as a number percentage. For example, in regards to a patient with IR measurements falling below 1.5 events/minute 50% of the time, % $IR_{<1.5}$ is expressed in the equation as 50, rather than 0.5. Solving the equation above, the POI risk percentage P may be expressed as:

$$P = \frac{e^{0.064(\%IR_{<1.5})-2.09(\Delta IR_{MEAN})-0.988}}{1 + e^{0.064(\%IR_{<1.5})-2.09(\Delta IR_{MEAN})-0.988}}.$$

Figure 7:
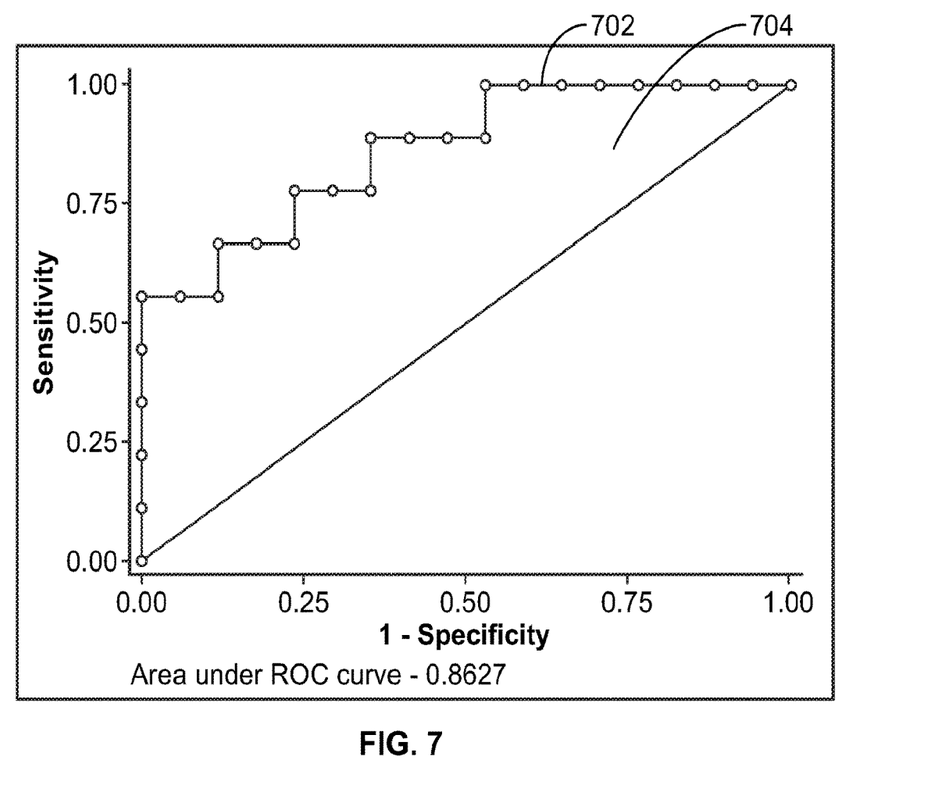
FIG. 7 depicts in accordance with various embodiments of the disclosure, a graphical illustration of the area under the curve for an experimental data set.

Referring now to FIG. 7, an ROC curve 702 that is based on the logit model is illustrated. The logit model accounts for: (1) the ratio of the mean IR value for POD#2 and the mean IR value for POD#1; and (2) the percentage below 1.5 metric. When applied to the experimental data, the ROC analysis shows an area 704 under the curve 702 of 0.86. This corresponds to a negative predictive value of 91.67%, and would allow an attending physician or other medical professional to rule out potential POI with nearly 92% certainty.

Thus, following surgery, one or more sensors may be immediately placed on the patient to begin obtaining IR measurements. At the end of POD#1, $IR_{MEAN1}$ is calculated. Alternatively, $IR_{MEAN1}$ is calculated as soon as two IR measurements are calculated on POD#1, and is then constantly updated throughout POD#1 as more IR measurements are obtained. The percentage of IR measurements below the 1.5 motility events per minute threshold is also calculated at the beginning of POD#1 and is continually updated. At the beginning of POD#2, $IR_{MEAN2}$ is calculated and updated in real-time, which thus allows $\Delta IR_{MEAN}$ to be calculated and updated in real-time. $\Delta IR_{MEAN}$ and the percentage of IR measurements below the 1.5 motility events per minute threshold are then used to calculate the risk percentage of developing POI. This POI risk percentage is constantly updated and can be monitored in real-time by the patient's healthcare provider.

Thus, by analyzing the IR data continuously collected from the patient following surgery, an assessment of POI risk can be provided. At step 108 of exemplary method 100, the POI risk P is reported. According to some embodiments, the POI risk is reported as a percentage between 0% and 100%, i.e. is reported as the result of the equation for P expressed above. This percentage may be expressed as either a number percentage (e.g. 50%) or as a decimal (e.g. 0.50). A lower percentage indicates the patient has a lower risk of developing (or having already developed) POI, while a higher percentage indicates the patient has a higher risk of developing POI. The POI risk is then used to determine an appropriate feeding protocol for the patient.

According to other embodiments, the POI risk assessment score is reported using a color system. A green light is used to indicate a low risk. A reported low risk indicates to the healthcare provider that it is ok to advance the patient's diet. A yellow light is used to indicate a medium risk. A reported medium risk indicates to the healthcare provider that they should "feed with caution" or proceed with similar treatment consistent with a borderline POI risk assessment. A red light is used to indicate a high risk. A reported high risk indicates to the healthcare provider that the patient should not be fed. In an exemplary embodiment, a low risk (i.e. a green light) corresponds to a POI risk percentage of about $P<0.33$. In an exemplary embodiment, a medium risk (i.e. a yellow light) corresponds to a POI risk percentage of about $0.33 \leq P<0.66$. In an exemplary embodiment, a high risk (i.e. a red light) corresponds to a POI risk percentage of $P \geq 0.66$.

In treating patients following surgery, it is generally desirable for both the healthcare provider and the patient to advance the patient to a standard diet as quickly as possible. This allows the patient to be discharged quicker following surgery, and can reduce costs and risks associated with lengthy hospital stays. A patient's postoperative diet may generally include a plurality of different stages. These stages include: (1) no food; (2) liquids; (3) soft foods such as JELL-O® or pudding; and (4) a standard diet. Advancing a patient too quickly through the different stages, particularly when the patient develops POI, can cause a variety of negative side-effects, including vomiting, pneumonia, etc., that require the healthcare provider to back the patient off the diet and prolong the patient's stay in the hospital.

The POI risk that is reported at step 108 can thus provide a healthcare provider with valuable information regarding when and how quickly to advance the patient through the example stages of a postoperative diet. A high risk may be indicated by a red light or a percentage above, for example, about 60% or higher, about 61% or higher, about 62% or higher, about 63% or higher, about 64% or higher, about 65% or higher or about 66.6%, and indicates to the healthcare provider that the patient should not be given any food. In an exemplary embodiment, a high risk, indicated by a red light or a percentage above about 66.6% in the example embodiments, indicates to the healthcare provider that the patient should not be given any food.

An intermediate risk may be indicated by a yellow light or a percentage between about 30%-60%, about 30%-62%, about 30%-64% or about 30%-65%, and indicates to the healthcare provider that the patient can be advanced to a liquid diet or a diet consisting of soft foods. In an exemplary embodiment, an intermediate risk, indicated by a yellow light or a percentage between about 33.3% and about 66.6%, indicates to the healthcare provider that the patient can be advanced to a liquid diet or a diet consisting of soft foods.

A low risk may be indicated by a green light or a percentage below about 30%, about 31%, about 32%, about 33% or about 34% and can indicate to the healthcare provider that the patient can be given a diet of solid foods. In an exemplary embodiment, a low risk, indicated by a green light or a percentage below about 33.3%, can indicate to the healthcare provider that the patient can be given a diet of solid foods. As the POI risk percentage is constantly updated, it can be used to indicate the stage of the diet at which the patient may safely be started at following surgery, or to indicate when it is safe to advance the patient to the next stage.

Another treatment that healthcare providers may utilize is the control of postoperative narcotic pain medicine. Narcotic pain medicine following surgery can contribute to bowel paralysis and the associated difficulty in advancing through the diet. As such, the reported POI risk percentage can help guide the healthcare provider in delivering an appropriate amount of narcotic pain medicine following surgery. High and intermediate risks, indicated by red and yellow lights respectively, generally indicate that the healthcare provider should either decline to start the patient on narcotic pain medicine, or reduce the amount of narcotic pain medicine being given to the patient. A low risk of POI, indicated by a green light, generally indicates to the healthcare provider that the patient can be started or maintained on narcotic pain medicine.

Figure 8:
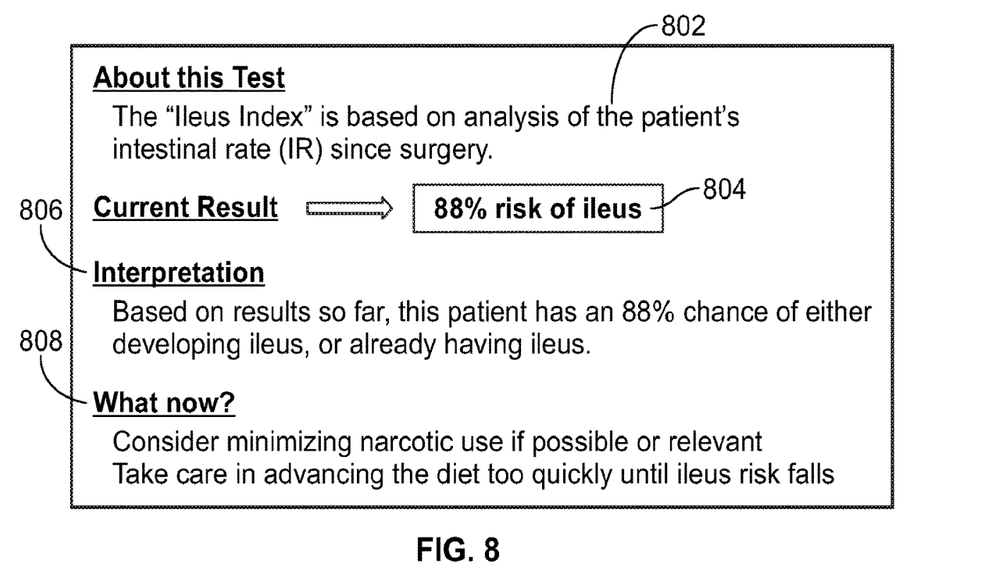
FIG. 8 depicts in accordance with various embodiments of the disclosure, an exemplary report including the patient's current risk of ileus.

According to some embodiments, the risk may be provided as a real-time report, providing an instantaneous ileus risk according to the analysis of the current IR data. FIG. 8 illustrates an exemplary report. At 802, the report includes a general description of the test. At 804, the patient's real-time ileus risk is displayed. At 806, according to some embodiments, an interpretation of the risk score is provided. At 808, potential treatment options for consideration by the attending physician or medical professional are displayed. The reporting format of FIG. 8 is exemplary only, and alternative reports may provide solely the POI risk prediction in a percentage, textual, stoplight, or other easily understandable format, alternatively, the POI risk along with a subset of other information may be provided in various embodiments of the disclosure.

According to some embodiments, the bedside computer or other processing device used to analyze the IR data is configured to display POI assessment reports on an internal display. Additionally or alternatively, the processor performing the IR analysis is communicatively coupled to a display device, such as a bedside patient monitoring display. In some embodiments, the report may be displayed on a monitor used to track other patient data, such as heart rate, blood pressure, and other vitals. In still other embodiments, the reporting data may be sent to an external computing device such as a PC, tablet, laptop, or smartphone, or shared across multiple devices capable of receiving reports. As yet another alternative, reports can be provided in email, text message, webpage, or other format and transmitted to one or more devices capable of receiving such messaging.

By applying the methods of the present disclosure, physicians may recommend or alter treatment according to the reported POI risk. In some embodiments, the POI assessment is reported as a negative predictive value, for example, a specific percentage value that a patient will not get POI. Significantly, a high negative predictive value would offer confidence to attending clinicians that POI is unlikely and therefore the patient's diet may be safely advanced.

According to some embodiments, the IR measurements and/or risk assessment data for the patient may be stored for later reference. The information may be stored locally, for example in memory associated with the processor, or it may be stored remotely, for example in a network database. Preferably, the information is stored in association with identifying information for the patient, such that it is available for later consideration if the same patient presents again for surgery and postoperative treatment. For example, a patient whose POI risk remained at a high level following a first surgery would likely not be advanced through the stages of the postoperative diet immediately following a second surgery. In addition, the patient would likely be provided with non-narcotic pain medicine. A patient whose POI risk was at a low level quickly following a first surgery, on the other hand, may be given a full meal immediately following surgery. This is a desirable outcome following surgery, as generally patients are simply monitored on POD#1, and not started on any diet until POD#2 when the POI risk can be determined. However, a previous indication of a low risk of POI following surgery can allow the healthcare provider to more quickly advance the patient through the stages of the diet, allowing the patient to be discharged quicker. For a repeat patient whose POI risk following a first surgery is known, it may be beneficial to observe the patient's mean IR value for POD#1 immediately following the second surgery. Thus, for this repeat patient, the calculation of the mean IR value for POD#1 may immediately calculated and updated in real-time following surgery, instead of waiting for the end of POD#1.

The present disclosure can play an important role in improving the recognition and management of POI. The current approach to evaluating POI is limited by non-standardized and imperfect methods. But the methods disclosed herein provide the capability to prospectively identify patients who will develop POI after surgery. The dynamic changes in IR early in the postoperative course, and percentage of time spent below a baseline IR level, are predictive of which patients are developing or will develop POI. Additionally, the methods herein yield a high negative predictive value that may offer surgeons further confidence to rule out POI and feed patients safely.

Each of these embodiments and obvious variations thereof is contemplated as falling within the spirit and scope of the present disclosure. Moreover, the present concepts expressly include any and all combinations and subcombinations of the preceding elements and aspects.

To provide aspects of the present disclosure, embodiments may employ any number of programmable processing devices that execute software or stored instructions. Physical processors and/or machines employed by embodiments of the present disclosure for any processing or evaluation may include one or more networked (Internet, cloud, WAN, LAN, satellite, wired or wireless (RF, cellular, WiFi, Bluetooth, etc.)) or non-networked general purpose computer systems, microprocessors, field programmable gate arrays (FPGAs), digital signal processors (DSPs), micro-controllers, smart devices (e.g., smart phones), computer tablets, handheld computers, and the like, programmed according to the teachings of the exemplary embodiments. In addition, the devices and subsystems of the exemplary embodiments can be implemented by the preparation of application-specific integrated circuits (ASICs) or by interconnecting an appropriate network of conventional component circuits. Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, database management software, and the like. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, processing capabilities may be distributed across multiple processors for better performance, reliability, cost, or other benefit.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read. Such storage media can also be employed to store other types of data, e.g., data organized in a database, for access, processing, and communication by the processing devices.

In various embodiments, the present application and invention further includes the subject matter of the following numbered clauses:

Clause 1. A method for assessing risk of post-operative ileus for a patient recovering from surgery, comprising: receiving, at least one processor, acoustic signal data from one or more sensors, each of the one or more sensors in contact with the patient and configured to capture acoustic signals from the abdominal cavity of the patient; analyzing, via the at least one processor, the acoustic signal data to determine one or more digestive metrics; determining a risk assessment score according to the one or more digestive metrics; and, displaying, via a display device communicatively coupled to the at least one processor, a report of potential post-operative ileus risk, the report comprising the risk assessment score.

Clause 2. The method of clause 1, wherein one of the one or more digestive metrics comprises the change in intestinal rate from postoperative day 1 to postoperative day 2.

Clause 3. The method of clause 1, wherein one of the one or more digestive metrics comprises the percentage of time spent below a threshold intestinal rate.

Clause 4. The method of clause 3, wherein the threshold intestinal rate is 1.5 motility events per minute.

Clause 5. The method of clause 1, wherein the risk assessment score is determined at least in part by application of receiver operating characteristic curve analysis.

Clause 6. The method of clause 1, wherein at least one of the one or more sensors adheres to the skin of the patient such that the at least one sensor is in contact with the abdominal region of the patient.

Clause 7. The method of clause 1, wherein at least one of the one or more sensors comprises an array of microelectric microphones.

Clause 8. The method of clause 1, wherein the acoustic signal data is received via wireless transmission.

Clause 9. The method of clause 1, wherein the acoustic signal data is received via wired transmission.

Clause 10. The method of clause 1, wherein the acoustic signal data is received from a network.

Clause 11. The method of clause 1, wherein the one or more sensors comprise a first sensor in contact with the left side of the abdominal region of the patient, and a second sensor in contact with the right side of the abdominal region of the patient.

Clause 12. The method of clause 1, wherein the risk assessment score comprises a percentage risk between 0 and 100 percent.

Clause 13. The method of clause 1, wherein the risk assessment score comprises one of low, medium, or high risk, and the displaying of the risk assessment score comprises a green light for low risk, a yellow light for medium risk, or a red light for high risk.

Clause 14. The method of clause 1, wherein the report is displayed in webpage format, and the display device is communicatively coupled to the at least one processor via a secure intranet.

Clause 15. The method of clause 1, wherein the report is displayed in webpage format, and the display device is communicatively coupled to the at least one processor via the Internet.

Clause 16. The method of clause 1, wherein the display device is a mobile device comprising a smart phone, laptop computer, or tablet.

Clause 17. The method of clause 1, wherein the report further comprises one or more recommended treatments consistent with the risk assessment score.

Clause 18. A method of determining risk of ileus for a patient following surgery, and administering a treatment according to the determined risk to expedite recovery for patients with lower predicted risk while reducing complications for patients with higher predicted risk, the method comprising: continuously measuring the intestinal rate of the patient over a fixed time period, the fixed time period comprising at least a period from the first post-operative day to the second post-operative day; analyzing the intestinal rate measurements to generate prediction data, the prediction data comprising a comparison of the median intestinal rate of the patient for the first post-operative day with the median intestinal rate of the patient for the second post-operative day; determining the expected risk of ileus for the patient according to the prediction data; administering an aggressive feeding protocol to the patient determined to have a lower expected risk, or restricting feeding to the patient determined to have a higher expected risk.

Clause 19. The method of clause 18, wherein the prediction data further comprises the percentage of time spent below a threshold intestinal rate.

Clause 20. The method of clause 19, wherein the threshold intestinal rate is 1.5 motility events per minute.

Clause 21. The method of clause 18, wherein the expected risk of ileus is determined at least in part by application of receiver operating characteristic curve analysis.

Clause 22. The method of clause 18, wherein the expected risk of ileus comprises a percentage risk between 0 and 100 percent.

Clause 23. The method of clause 18, wherein the expected risk of ileus is reported as a red light indicating higher expected risk, or a green light indicating lower expected risk.

Clause 24. The method of clause 23, wherein the reporting further comprises one or more recommended treatments consistent with the expected risk of ileus.

Clause 25. The method of clause 18, wherein the determination of expected risk is relative to a threshold risk value, and the threshold risk value is configurable.

Clause 26. A method of determining risk of ileus for a patient following surgery, and administering a treatment according to the determined risk to expedite recovery for patients with lower predicted risk while reducing complications for patients with higher predicted risk, the method comprising: attaching one or more sensors to the patient; continuously measuring, using the one or more sensors, an intestinal rate of the patient luring a first postoperative day to obtain a first plurality of intestinal rate measurements; determining a first mean intestinal rate value for the first postoperative day based on the first plurality of intestinal rate measurements; continuously measuring, using the one or more sensors, the intestinal rate of the patient during a second postoperative day to obtain a second plurality of intestinal rate measurements; determining a second mean intestinal rate value for the second postoperative day based on the second plurality of intestinal rate measurements; calculating a change in mean intestinal rate value based on the first mean intestinal rate value and the second mean intestinal rate value; analyzing the first plurality of intestinal rate measurements and the second plurality of intestinal rate measurements to calculate a percentage of intestinal rate measurements below a threshold intestinal rate; determining the risk of ileus for the patient according to at least the calculated change in mean intestinal rate and the calculated percentage of intestinal rate measurements below the threshold intestinal rate; continuously updating the determined risk of ileus for the patient; administering an aggressive feeding protocol to the patient determined to have a lower expected risk of ileus, or a restricting feeding protocol to the patient determined to have a higher expected risk of ileus.

EXAMPLE

The following example is not intended to limit the scope of the claims to the invention, but is rather intended to be exemplary of certain embodiments. Any variations in the exemplified methods which occur to the skilled artisan are intended to fall within the scope of the present invention.

In order to develop the methods disclosed herein, analysis was performed using patient IR data from a previously performed study. For context, a summary of the prior study is first provided below, followed by a discussion of the analysis performed using the IR data.

Study Overview

Using an AGIS biosensor,[15] a blinded, prospective, longitudinal cohort study was performed to measure intestinal motility rates in patients recovering from abdominal surgery. The study consecutively recruited inpatients undergoing abdominal surgery at Cedars-Sinai Medical Center (CSMC), the West Los Angeles Veteran Administration (WLAVA) Medical Center, and Ronald Reagan UCLA Medical Center. Four different colorectal surgeons performed the operations. Patients were eighteen years of age or older, able to provide informed consent, and recovering from abdominal surgery.

Figure 9:
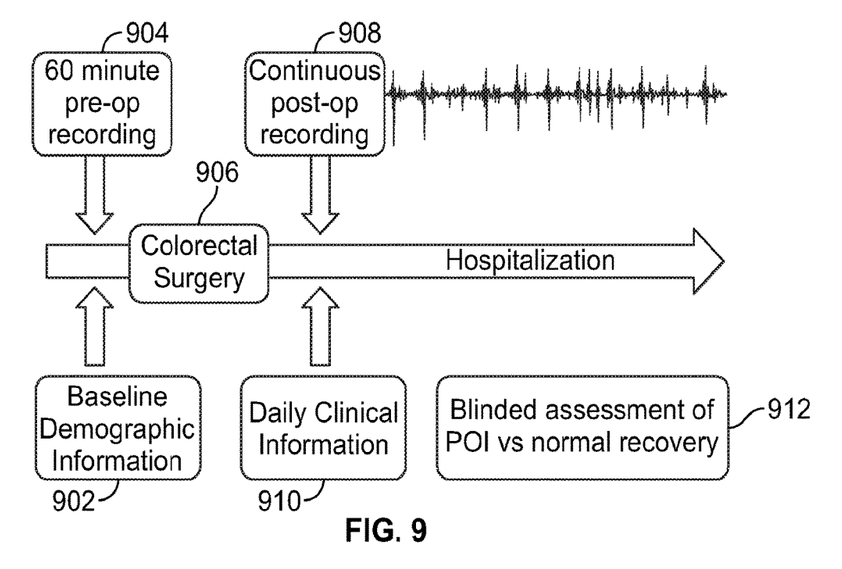
FIG. 9 depicts in accordance with various embodiments of the disclosure, a timeline for collection of patient data.

Referring now to FIG. 9, prior to surgery, baseline demographic information 902 and a 60-minute baseline preoperative acoustic recording 904 were obtained for each subject. The surgeon then re-applied the monitoring system upon completion of the operation 906, and recordings 908 continued until discharge, or until the patient opted to remove the sensors.

All patients, health care providers, and members of the clinical research team were blinded to the results of the monitoring. The data were stored and submitted to the electrical engineering team at UCLA who analyzed the recordings using specialized software to generate IR values in events/minute for each subject.[15] The engineering team was blinded to all clinical data.

As shown in 912, members of the research team who were blinded to sensor results monitored and recorded clinical information, including age, gender, race, and body mass index (BMI). The indications for surgery, types of surgery performed, surgical techniques, and any documented operative complications were also recorded. Monitoring of daily clinical assessments 910, including symptoms (nausea, vomiting, and abdominal pain), flatus, bowel movements, diet, ambulation, medication use, and length of hospitalization was performed. If abdominal imaging was performed at the discretion of the surgical team, then that information was also recorded in the clinical records.

Patients were classified into those who developed POI during the postoperative course vs. those without POI who, by definition, experienced uneventful GI recovery. Although POI has many definitions in the literature, a pragmatic definition of POI was applied here, and includes presence of one or more of the following: (1) postoperative nausea or vomiting that precluded advancement of diet or led to regression of diet; (2) Symptoms that led to the need for nasogastric tube placement for decompression.

All patients received a standardized feeding protocol as part of usual care for each participating hospital. There were differences in the standard protocol among the participating hospitals. For UCLA and WLAVA, the protocol included ice chips on postoperative day (POD) zero, sips of clear liquids on POD#1 (not to exceed 60 cc per hour), clear liquid diet on POD#2, and advancement to regular diet on POD#3. For CSMC the standard protocol was more aggressive, with initiation of clear liquids on POD zero, and rapid progression to a regular diet by the morning POD#1 in patients without early clinical evidence of POI. Regardless of hospital, patients intolerant of the feeding protocol, including nausea or vomiting precluding advancement, or those that developed significant abdominal distension, fell off the feeding protocol.

Figure 10:
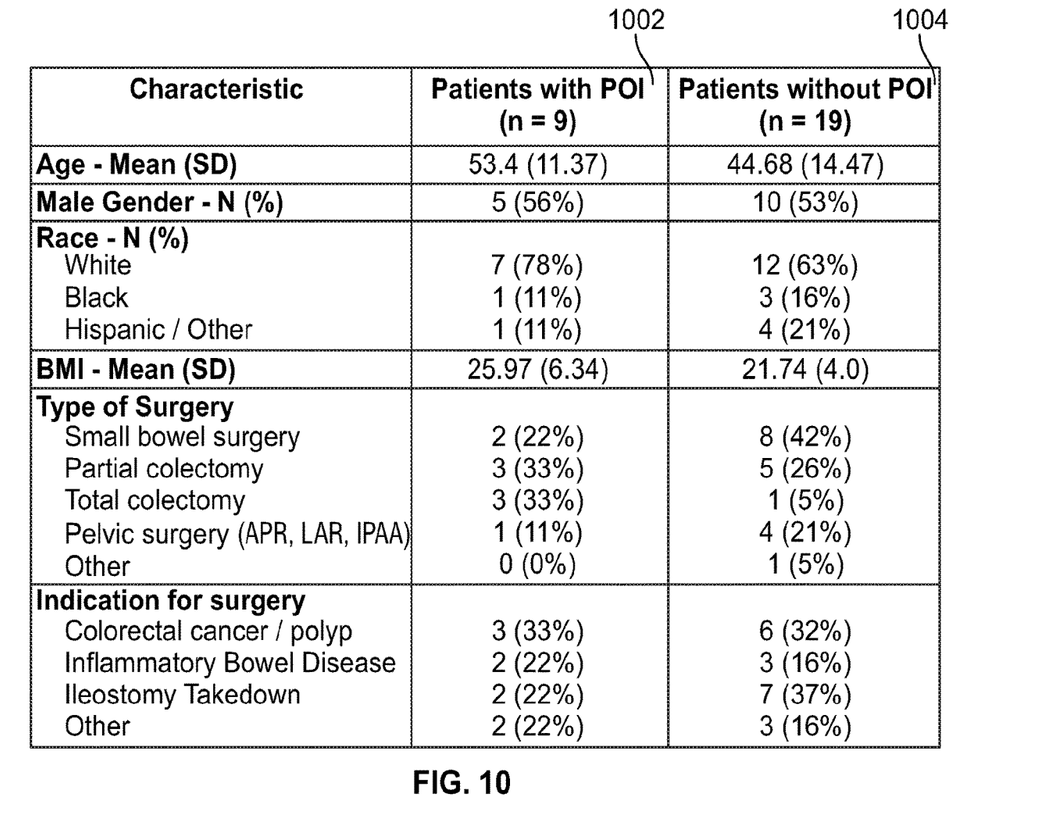
FIG. 10 depicts in accordance with various embodiments of the disclosure, patient characteristics for a study performed to measure intestinal rate (IR) in patients recovering from abdominal surgery.

28 patients participated in the study, of whom 9 developed POI during their postoperative course. FIG. 10 provides a summary of patient characteristics for the POI group 1002 and the non-POI group 1004. The types of surgeries performed were categorized into the following groups: small bowel surgeries (36%), partial colectomies (29%), total colectomies (14%), pelvic surgeries (18%) and other types (4%) that did not fall into any of these categories. The indications for surgery were colorectal cancer/unresectable polyp (32%), ileostomy takedowns (32%), inflammatory bowel disease (IBD) (18%), small bowel obstruction (7%), diverticulitis (4%), perineal wound (4%) and chronic constipation (4%).

Prospective Analysis of POI Risk

The hypothesis was that a method could be developed to use computer-analyzed bowel sounds to accurately separate patients with POI vs. uneventful GI recovery at an early postoperative stage. To that end, an automated prediction method was developed that informs surgeons and nurses about the probability of a patient developing POI. In the sections that follow, the analyses employed to develop the method and evaluate its predictive accuracy is described, as applied to patients recovering from abdominal surgery. All analyses were conducted using Stata v10 (Stata Corp, College Station, Tex.).

Using the study data, a comparison was performed of the postoperative median IR values between the POI and non-POI groups using the Wilcoxon rank sum test, as IR was non-normally distributed. Then, each time segment was examined, starting with preoperative IR, and then comparing median IR on POD zero through POD#4, in search of the earliest point that IR diverged between POI vs. non-POI groups. Using receiver operator characteristic (ROC) curve analysis, a method was identified that maximized predictive discrimination between POI vs. non-POI groups. The ROC-defined threshold was applied to calculate the sensitivity, specificity, and negative predictive value (NPV) of the method in distinguishing between groups. NPV was emphasized because a high NPV could rule-out POI; that is, a achieving a high NPV could offer confidence to surgeons and nurses that POI is unlikely and diet advancement may be safe.

Comparisons of Intestinal Rates Between Groups

Figure 11:
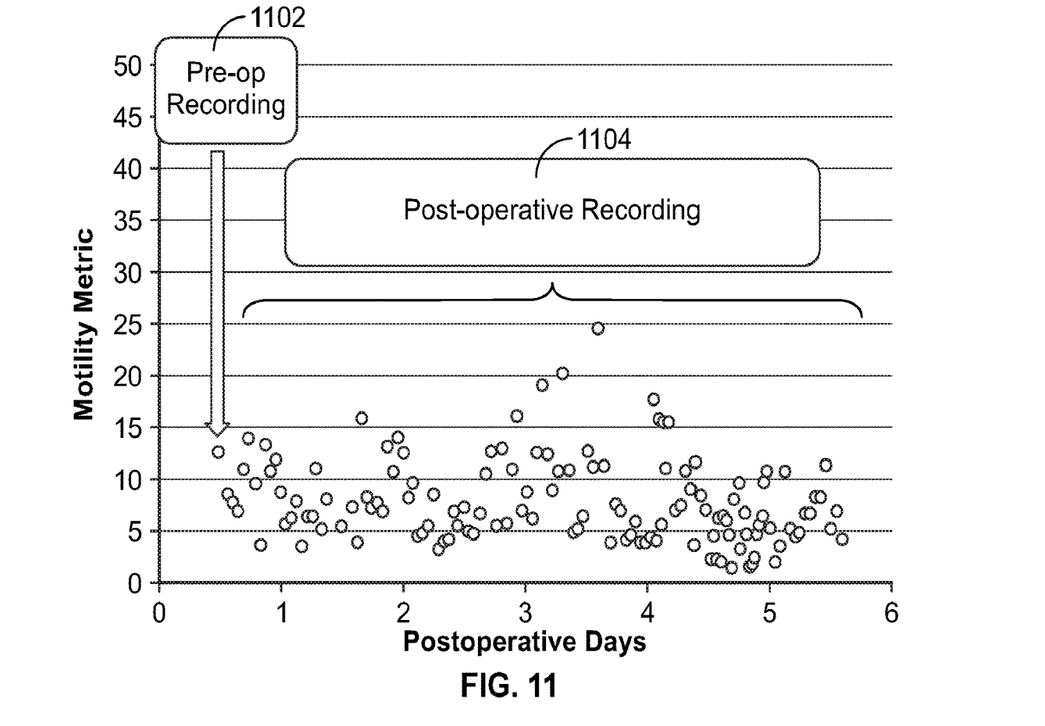
FIG. 11 depicts in accordance with various embodiments of the disclosure, a chart of intestinal rate by postoperative day for a patient experiencing normal bowel recovery.
Figure 12:
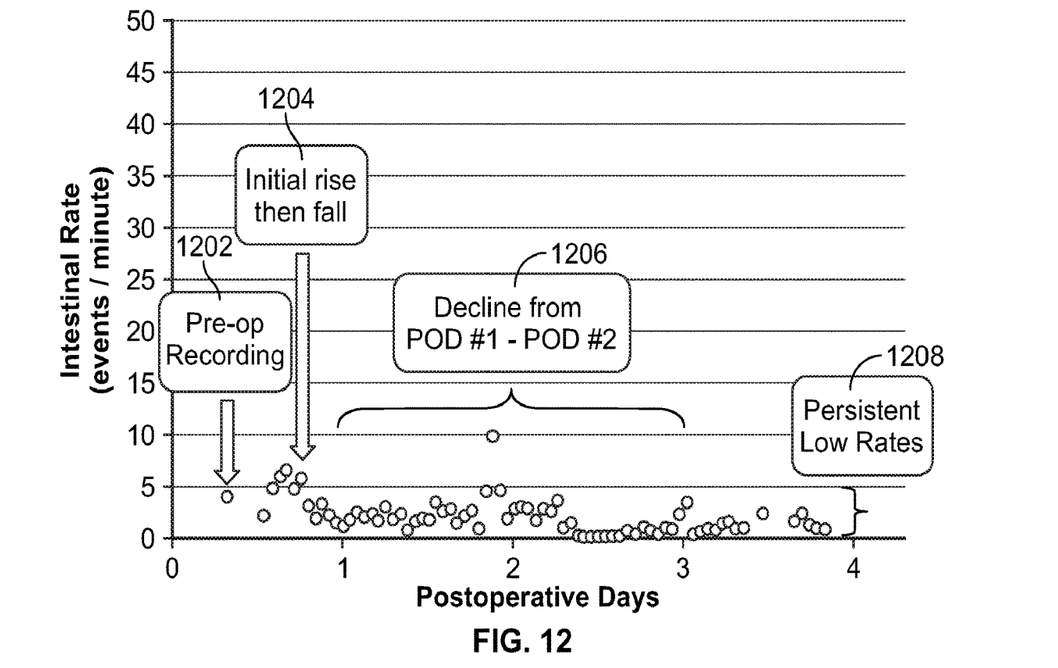
FIG. 12 depicts in accordance with various embodiments of the disclosure, a chart of intestinal rate by postoperative day for a patient experiencing severe postoperative ileus.

FIG. 11 shows an IR tracing for a patient without POI, including preoperative recording 1102 and postoperative recordings 1104. FIG. 12 shows an IR tracing for a patient with POI, including preoperative recordings 1202. The POI tracing shows an initial rise 1204 in IR measurements on POD#1, followed by a decline 1206 in IR measurements on POD#2. Moreover, the IR measurements are consistently low as compared to the non-POI tracing of FIG. 11.

Figure 13:
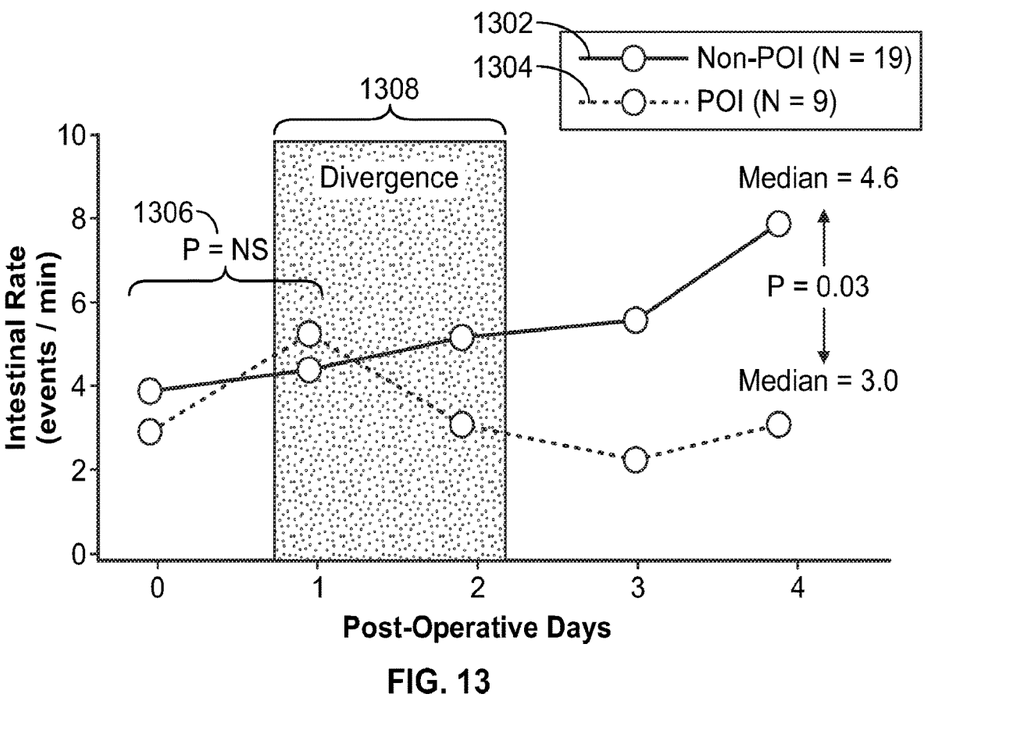
FIG. 13 depicts in accordance with various embodiments of the disclosure, a chart of intestinal rate by postoperative day for the non-POI patients and POI patients in the study group.
Figure 14:
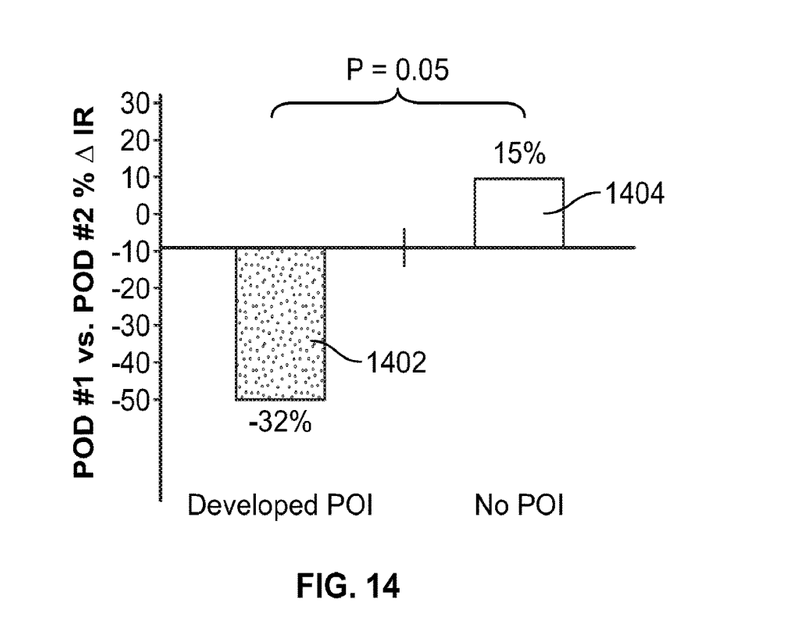
FIG. 14 depicts in accordance with various embodiments of the disclosure, a comparison of the percentage change in intestinal rate, from postoperative day 1 to postoperative day 2, for the POI and non-POI patient groups.

FIG. 13 charts the median IR by POD for the POI group 1302 and the non-POI group 1304. Over the entire postoperative course, the median IR in the POI group was significantly lower (3.0 events/minute) than in the non-POI group (4.6 events/minute) (P=0.03); these results are consistent with previous work indicating that IR data significantly distinguishes POI from non-POI.[15] As can be seen in FIG. 13 at 1306, the IR was significantly different between groups on POD#0 and POD#1. However, between POD#1 and POD#2 there was a divergence in IR curves between groups. When examining the rate of IR change 1308 between POD#1 and POD#2, there was a significant difference between POI and non-POI groups; whereas POI patients had a 32% drop in IR between days, non-POI patients had a 15% increase during the same time period (p=0.05). This difference is further illustrated in FIG. 14, where the 32% drop 1402 for the POI group and the 15% increase for the non-POI group.

As an additional metric to distinguish between POI vs. non-POI groups, an examination was made of the percentage of time each subject had an IR below the 5$^{th}$ percentile—namely, below a floor of 1.5 motility events/minute. Whereas patients with POI spent 40% of their postoperative course below this threshold, patients without POI spent only 22% of their time below 1.5 events/minute (P=0.007).

Receiver Operating Characteristic (ROC) Curve Analysis

The analysis shows that both the POD#1 vs. POD#2 IR change, and the percentage of time spent below an IR of 1.5/minute, potentially distinguishes POI from non-POI. Therefore, both terms were entered into a logit model used to predict POI. The area under the resulting ROC curve was 0.83. Using a threshold value of 0.4 to define a "positive" test (that is, if the method predicts ≥40% chance of POI, then consider the test positive), the resulting sensitivity, specificity, and NPV were 63%, 72%, and 81%. In other words, if the test is negative, then the surgeon could rule-out POI with 81% certainty according to this sample of data.

The prediction accuracy (as expressed by NPV) can be adjusted further by adjusting the threshold values used for the analysis. For example, to further promote safety considerations, and avoid aggressive feeding for a patient who seems to be getting possible POI, the analysis can be adjusted to generate a very high negative predictive value to rule out POI through adjustment of threshold settings. In one example, by setting the threshold to require a 60% drop in IR between POD1 and POD2, the NPV for this one-factor analysis is 87%. In other words, if a patient does not drop by 60% between POD#1 and POD#2, there is an 87% chance that the patient is NOT going to get POI.

Additional analysis may be performed with further patient data sets, to fine tune the threshold settings and further verify the prospective use of the method to identify POI risk.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

REFERENCES

1. Doorly M G, Senagore A J. Pathogenesis and clinical and economic consequences of postoperative ileus. Surg Clin North Am 2012; 92:259-72, viii.
2. Lubawski J, Saclarides T. Postoperative ileus: strategies for reduction. Ther Clin Risk Manag 2008; 4:913-7.
3. Kehlet H, Holte K. Review of postoperative ileus. Am J Surg 2001; 182:3S-10S.
4. Asgeirsson T. Postoperative ileus: it costs more than you expect. J Am Coll Surg 2010; 210:228-31.
5. Prasad M, Matthews J B. Deflating postoperative ileus. Gastroenterology 1999; 117:489-92.
6. Lewis S J, Egger M, Sylvester P A, et al. Early enteral feeding versus "nil by mouth" after gastrointestinal surgery: systematic review and meta-analysis of controlled trials. BMJ 2001; 323:773-6.
7. Andersen H K, Lewis S J, Thomas S. Early enteral nutrition within 24 h of colorectal surgery versus later commencement of feeding for postoperative complications. Cochrane Database Syst Rev 2006:CD004080.

8. Lewis S J, Andersen H K, Thomas S. Early enteral nutrition within 24 h of intestinal surgery versus later commencement of feeding: a systematic review and meta-analysis. J Gastrointest Surg 2009; 13:569-75.
9. Warren J, Bhalla V, Cresci G. Postoperative diet advancement: surgical dogma vs evidence-based medicine. Nutr Clin Pract 2011; 26:115-25.
10. Wolff B G, Viscusi E R, Delaney C P, et al. Patterns of gastrointestinal recovery after bowel resection and total abdominal hysterectomy: pooled results from the placebo arms of alvimopan phase III North American clinical trials. J Am Coll Surg 2007; 205:43-51.
11. Iyer S, Saunders W B, Stemkowski S. Economic burden of postoperative ileus associated with colectomy in the United States. J Manag Care Pharm 2009; 15:485-94.
12. Asgeirsson T, El-Badawi K I, Mahmood A, et al. Postoperative ileus: it costs more than you expect. J Am Coll Surg 2010; 210:228-31.
13. Barletta J F, Senagore A J. Reducing the Burden of Postoperative ileus: Evaluating and Implementing an Evidence-based Strategy. World J Surg 2014.
14. Muller S, Zalunardo M P, Hubner M, et al. A fast-track program reduces complications and length of hospital stay after open colonic surgery. Gastroenterology 2009; 136: 842-7.
15. Spiegel B M, Kaneshiro M, Russell M M, et al. Validation of an acoustic gastrointestinal surveillance biosensor for postoperative ileus. J Gastrointest Surg 2014; 18:1795-803.

The invention claimed is:

1. A method for assessing risk of post-operative ileus for a patient recovering from surgery, comprising:
receiving, by at least one processor, acoustic signal data from one or more sensors, each of the one or more sensors configured to be in contact with the patient and configured to capture acoustic signals from the abdominal cavity of the patient;
analyzing, via the at least one processor, the acoustic signal data to continuously measure an intestinal rate of the patient over a fixed time period, the fixed time period comprising at least a period comprising at least a period from a first post-operative day to a second post-operative day;
calculating a change in mean intestinal rate between a first mean intestinal rate for the first post-operative day and a second mean intestinal rate for the second post-operative day;
calculating a percentage of intestinal rate measurements below a threshold intestinal rate during the fixed time period;
determining, via the at least one processor, a risk assessment score based on both the change in mean intestinal rate and the percentage of intestinal rate measurements below the threshold intestinal rate;
displaying, via a display device communicatively coupled to the at least one processor, a report of potential post-operative ileus risk, the report comprising the risk assessment score;
administering (i) an aggressive feeding protocol to the patient in response to determining that the patient has a lower risk assessment score, or (ii) a restricted feeding protocol to the patient in response to determining that the patient has a higher risk assessment score.

2. The method of claim 1, wherein the threshold intestinal rate is 1.5 motility events per minute.

3. The method of claim 1, further comprising determining a risk assessment score according to both the change in mean intestinal rate and the percentage of intestinal rate measurements below the threshold intestinal rate, wherein the risk assessment score is determined at least in part by application of receiver operating characteristic curve analysis.

4. The method of claim 1, wherein at least one of the one or more sensors are configured to adhere to the skin of the patient such that the at least one sensor is in contact with the abdominal region of the patient.

5. The method of claim 1, wherein at least one of the one or more sensors comprises an array of microelectric microphones.

6. The method of claim 1, wherein the acoustic signal data is received via wireless transmission.

7. The method of claim 1, wherein the acoustic signal data is received via wired transmission.

8. The method of claim 1, wherein the acoustic signal data is received from a network.

9. The method of claim 1, wherein the one or more sensors comprise a first sensor configured to be in contact with the left side of the abdominal region of the patient, and a second sensor configured to be in contact with the right side of the abdominal region of the patient.

10. The method of claim 3, wherein the risk assessment score comprises a percentage risk between 0 and 100 percent.

11. The method of claim 3, wherein the risk assessment score comprises one of low, medium, or high risk, and the displaying of the risk assessment score comprises a green light for low risk, a yellow light for medium risk, or a red light for high risk.

12. The method of claim 1, wherein the report is displayed in webpage format, and the display device is communicatively coupled to the at least one processor via a secure intranet.

13. The method of claim 1, wherein the report is displayed in webpage format, and the display device is communicatively coupled to the at least one processor via the Internet.

14. The method of claim 1, wherein the display device is a mobile device comprising a smart phone, laptop computer, or tablet.

15. The method of claim 3, wherein the report further comprises one or more recommended treatments consistent with the risk assessment score.

16. The system of claim 1, wherein the risk assessment score is determined based on the following equation, wherein $\%_{IR<1.5}$ is the calculated percentage of intestinal rate measurements below the threshold intestinal rate, and wherein $\Delta IR_{MEAN}$ is the calculated change in mean intestinal rate:

$$P = \frac{e^{0.064(\%IR_{<1.5})-2.09(\Delta IR_{MEAN})-0.988}}{1+e^{0.064(\%IR_{<1.5})-2.09(\Delta IR_{MEAN})-0.988}}.$$

17. A method for assessing risk of post-operative ileus for a patient recovering from surgery, comprising:
receiving, by at least one processor, acoustic signal data from one or more sensors, each of the one or more sensors being configured to capture acoustic signals from the abdominal cavity of the patient;
analyzing, via the at least one processor, the acoustic signal data to measure an intestinal rate of the patient over a fixed time period, the fixed time period comprising at least a period comprising at least a period from a first post-operative day to a second post-operative day;

calculating a change in mean intestinal rate between a first mean intestinal rate for the first post-operative day and a second mean intestinal rate for the second post-operative day;

determining, via the at least one processor, a risk assessment score based at least on the change in mean intestinal rate between the first mean intestinal rate for the first post-operative day and the second mean intestinal rate for the second post-operative day;

administering (i) an aggressive feeding protocol to the patient in response to determining that the patient has a lower risk assessment score, or (ii) a restricted feeding protocol to the patient in response to determining that the patient has a higher risk assessment score.

18. A method for assessing risk of post-operative ileus for a patient recovering from surgery, comprising:

receiving, by at least one processor, acoustic signal data from one or more sensors, each of the one or more sensors being configured to capture acoustic signals from the abdominal cavity of the patient;

analyzing, via the at least one processor, the acoustic signal data to measure an intestinal rate of the patient over a fixed time period, the fixed time period comprising at least a period comprising at least a period from a first post-operative day to a second post-operative day;

calculating a percentage of intestinal rate measurements below a threshold intestinal rate during the fixed time period;

determining, via the at least one processor, a risk assessment score based at least on the percentage of intestinal rate measurements below the threshold intestinal rate;

administering (i) an aggressive feeding protocol to the patient in response to determining that the patient has a lower risk assessment score, or (ii) a restricted feeding protocol to the patient in response to determining that the patient has a higher risk assessment score.

* * * * *